US011007452B2

(12) United States Patent
Blum et al.

(10) Patent No.: US 11,007,452 B2
(45) Date of Patent: May 18, 2021

(54) PROCESS AND SYSTEM FOR DEHYDRATING A PRODUCT STREAM IN ETHANOL PRODUCTION

(71) Applicant: WHITEFOX TECHNOLOGIES LIMITED, London (GB)

(72) Inventors: Stephan Rüdiger Blum, Calgary (CA); Virginia Andrade, Calgary (CA)

(73) Assignee: WHITEFOX TECHNOLOGIES LIMITED, London (GB)

(*) Notice: Subject to any disclaimer, the term of this patent is extended or adjusted under 35 U.S.C. 154(b) by 0 days.

(21) Appl. No.: 16/694,087

(22) Filed: Nov. 25, 2019

(65) Prior Publication Data

US 2020/0086227 A1    Mar. 19, 2020

Related U.S. Application Data

(63) Continuation of application No. 15/400,546, filed on Jan. 6, 2017, now Pat. No. 10,486,079.
(Continued)

(51) Int. Cl.
*B01D 3/00* (2006.01)
*B01J 20/18* (2006.01)
(Continued)

(52) U.S. Cl.
CPC ............. *B01D 3/002* (2013.01); *B01D 3/007* (2013.01); *B01D 3/06* (2013.01); *B01D 3/145* (2013.01);
(Continued)

(58) Field of Classification Search
CPC .......... B01D 3/007; B01D 3/06; B01D 3/145; B01D 3/148; B01D 3/322; B01D 15/203;
(Continued)

(56) References Cited

U.S. PATENT DOCUMENTS 4,217,178 A    8/1980 Katzen et al.
4,306,942 A    12/1981 Brush et al.
(Continued)

FOREIGN PATENT DOCUMENTS

JP    2016047530    4/2016
WO    2016088134    6/2016

OTHER PUBLICATIONS

Roy, Christian; "Vaperma Siftek Membrane for Ethanol Refining: A General Presentation"; Vaperma, Inc.; Mar. 2010; (32 pages).
(Continued)

*Primary Examiner* — Brian A McCaig
(74) *Attorney, Agent, or Firm* — K&L Gates LLP

(57) ABSTRACT

The present disclosure provides processes and systems for dehydrating a byproduct stream in ethanol production. In one embodiment, a feed mixture is distilled with one or more distillation units to remove at least a portion of the water, and form a first byproduct stream. The first byproduct stream is contacted with a molecular sieve unit, thereby forming a product stream. The molecular sieve unit is cyclically contacted with at least a portion of the product stream to regenerate the molecular sieve unit and form one or more regenerate streams. A second byproduct stream including at least one of (1) the regenerate streams and (2) at least a portion of the fusel oil stream is contacted with a separation system, thereby forming a permeate and a retentate. At least a portion of the retentate is forwarded into the product stream.

23 Claims, 7 Drawing Sheets

Related U.S. Application Data

(60) Provisional application No. 62/432,008, filed on Dec. 9, 2016, provisional application No. 62/276,318, filed on Jan. 8, 2016.

(51) Int. Cl.
    *B01J 20/34*         (2006.01)
    *C07C 29/80*        (2006.01)
    *B01D 3/14*          (2006.01)
    *B01D 3/06*          (2006.01)
    *B01D 61/36*        (2006.01)
    *B01D 3/32*          (2006.01)
    *B01D 53/26*        (2006.01)
    *B01D 15/20*        (2006.01)

(52) U.S. Cl.
    CPC .............. *B01D 3/148* (2013.01); *B01D 3/322* (2013.01); *B01D 15/203* (2013.01); *B01D 53/261* (2013.01); *B01D 61/364* (2013.01); *B01J 20/18* (2013.01); *B01J 20/3408* (2013.01); *B01J 20/3475* (2013.01); *C07C 29/80* (2013.01); *B01D 2311/2626* (2013.01); *B01D 2311/2669* (2013.01)

(58) Field of Classification Search
    CPC ................ B01D 15/261; B01D 61/364; B01D 2311/2626; B01D 2311/2669; B01J 20/18; B01J 20/3408; B01J 20/3475; C07C 29/80
    See application file for complete search history.

(56) References Cited

U.S. PATENT DOCUMENTS

| | | |
|---|---|---|
| 4,326,036 A | 4/1982 | Hayes |
| 4,340,446 A | 7/1982 | Crawford |
| 4,405,409 A | 9/1983 | Tusel et al. |
| 4,407,662 A | 10/1983 | Ginder |
| 4,442,210 A * | 4/1984 | Dessau ............... C07C 29/76 435/161 |
| 4,978,430 A | 12/1990 | Nakagawa et al. |
| 5,105,029 A | 4/1992 | Ninomiya et al. |
| 5,124,004 A | 6/1992 | Grethlein et al. |
| 7,470,348 B2 | 12/2008 | Seiki et al. |
| 7,572,353 B1 | 8/2009 | Vander Griend |
| 7,594,981 B2 | 9/2009 | Ikeda |
| 7,699,961 B2 | 4/2010 | Ikeda et al. |
| 7,732,173 B2 | 6/2010 | Mairal et al. |
| 7,744,727 B2 | 6/2010 | Blum et al. |
| 7,922,872 B2 | 4/2011 | Kihara et al. |
| 8,128,787 B2 | 3/2012 | Wynn et al. |
| 8,128,826 B2 | 3/2012 | Plante et al. |
| 8,129,573 B2 | 3/2012 | Kikuchi et al. |
| 8,142,662 B2 | 3/2012 | Osora et al. |
| 8,425,734 B2 | 4/2013 | Goel et al. |
| 8,585,904 B2 | 11/2013 | Osora et al. |
| 8,858,798 B2 | 10/2014 | Osora et al. |
| 9,149,769 B2 | 10/2015 | Seiki et al. |
| 9,194,623 B2 | 11/2015 | Kihara et al. |
| 9,925,476 B2 | 3/2018 | Crawford et al. |
| 10,118,107 B1 | 11/2018 | Kwik et al. |
| 2007/0000769 A1 | 1/2007 | Brown |
| 2007/0131533 A1 | 6/2007 | Blum et al. |
| 2008/0135396 A1 | 6/2008 | Blum |
| 2008/0020795 A1 | 8/2008 | Plante et al. |
| 2008/0207959 A1 | 8/2008 | Plante et al. |
| 2009/0057128 A1 | 3/2009 | Vane et al. |
| 2009/0117631 A1 | 5/2009 | Cote et al. |
| 2009/0215139 A1 | 8/2009 | Datta et al. |
| 2009/0301970 A1 | 12/2009 | Noel |
| 2010/0051441 A1 | 3/2010 | Vane et al. |
| 2010/0219128 A1 | 9/2010 | Seiki et al. |
| 2010/0314320 A1 | 12/2010 | Osora et al. |
| 2011/0130598 A1 | 6/2011 | Huang et al. |
| 2011/0315541 A1 | 12/2011 | Xu |
| 2013/0309738 A1* | 11/2013 | Barr ..................... C12M 45/04 435/160 |
| 2015/0087041 A1 | 3/2015 | Parten |
| 2016/0107964 A1 | 4/2016 | Matsukata et al. |
| 2017/0203230 A1 | 7/2017 | Raiser |
| 2017/0204030 A1 | 7/2017 | Maeda et al. |

OTHER PUBLICATIONS

Gabardo, Helio "Dehydration of Ethanol Via Membrane Polymeric Siftek", Dec. 4, 2009 (34 pages).

* cited by examiner

PROCESS AND SYSTEM FOR DEHYDRATING A PRODUCT STREAM IN ETHANOL PRODUCTION

REFERENCE TO PENDING PRIOR PATENT APPLICATIONS

This patent application is a continuation of U.S. patent application Ser. No. 15/400,546 filed on Jan. 6, 2017 which claims the benefit of U.S. Provisional Patent Application No. 62/432,008, filed on Dec. 9, 2016, and U.S. Provisional Patent Application No. 62/276,318, filed on Jan. 8, 2016, the entire contents of each of which are hereby incorporated herein by reference.

BACKGROUND

Various processes and systems have been used for producing ethanol from feedstock. For example, in some prior systems, ethanol is produced by fermentation, yielding a stillage (beer) with an ethanol concentration of up to 18%, which is subsequently concentrated in three steps: (1) distillation in a beer column, increasing the ethanol concentration up to 65%, followed by (2) processing in a stripper/rectifier column further increasing the ethanol concentration to around 90 vol %, and (3) a molecular-sieve-based dehydration (also referred to as pressure swing adsorption) to a target ethanol concentration of 99.0 to 99.95 vol %. In the stripper/rectifier column, a mixture of high boiling components including propanol, butanol, and isomeric pentanols (also referred to as fusel oil) needs to be removed in a side draw to avoid accumulation therein.

SUMMARY

According to one non-limiting aspect of the present disclosure, an example embodiment of a method of dehydrating a byproduct stream in ethanol production is described. The example method includes distilling a feed mixture including ethanol and water with one or more distillation units to remove at least a portion of the water, and form a distillation unit bottom stream, a vaporous overhead stream, and a fusel oil stream. A molecular sieve unit is contacted with a first byproduct stream including at least one selected from a portion of the vaporous overhead stream and a portion of the fusel oil stream, thereby forming a product stream. The molecular sieve unit is cyclically contacted with at least a portion of the product stream to regenerate the molecular sieve unit and form one or more regenerate streams. A second byproduct stream including at least one of (1) the regenerate stream and (2) at least a portion of the fusel oil stream is contacted with a separation system, thereby forming a permeate and a retentate. At least a portion of the permeate is forwarded into the second byproduct stream. Heat is exchanged between at least a portion of the retentate and at least one selected from the feed mixture, the distillation unit bottom stream, the first byproduct stream, and a portion of the regenerate streams.

In certain non-limiting embodiments of the method, a scrubbing system is used to remove ethanol from vent gases (e.g., $CO_2$, with traces of ethanol) from the fermentation stream separating the ethanol from $CO_2$ before venting to the atmosphere. Scrubber water is added in the scrubbing system generating a water stream containing small amounts of ethanol which is directed to the beer well prior to being fed to the beer column. At least a portion of the product stream is forwarded to a flash vessel, thereby forming a vent stream. A second byproduct stream including at least one of (1) a portion of the regenerate streams, (2) a portion of the first byproduct stream, (3) a portion of the fusel oil stream, (4) a portion of the vent stream and (5) a portion of the scrubber water stream is contacted with a separation system, thereby forming a permeate, a retentate, and a stripper unit bottom stream. In certain non-limiting embodiments of the method, at least a portion of the permeate is forwarded into the second byproduct stream. Heat is exchanged between at least a portion of the retentate and at least one selected from the feed mixture, the distillation unit bottom streams, the first byproduct stream, evaporators and a portion of the regenerate streams.

In certain non-limiting embodiments of the method, heat is exchanged between at least a portion of the stripper unit bottom stream and at least one selected from the group consisting of the feed mixture, the distillation unit bottom streams, the first byproduct stream, and a portion of the regenerate streams. According to another non-limiting aspect of the present disclosure, heat is exchanged between at least a portion of at least one of the regenerate streams and at least one selected from the feed mixture, the distillation unit bottom streams, and the first byproduct stream.

According to another non-limiting aspect of the present disclosure, steam generated in at least one of (1) evaporators, (2) a hydroheater, and (3) a boiler is injected to the distillation units as energy source for their operation. The steam injected in the distillation units increases the water content and dilutes the solids contained in the distillation unit bottom streams. The solids in distillation unit bottom streams are recovered in at least one selected from a centrifuge, a dryer, and the evaporators. In certain non-limiting embodiments of the method, at least a portion of the steam injected on the distillation units is replaced by reboiling at least one selected from a portion of the beer column stillage stream and the stripper-rectifier bottom stream. In certain non-limiting embodiments of the method, the energy displaced in the distillation units by forwarding at least a portion of the regenerate streams into the second byproduct stream allows to forward (1) at least a portion of the steam from the hydroheater into the evaporators, and (2) steam from the evaporators to the distillation units.

According to another non-limiting aspect of the present disclosure, an example embodiment of a system for dehydrating a byproduct stream in ethanol production is described. The system includes one or more distillation units configured to receive a feed mixture including ethanol and water, to remove at least a portion of the water, and to form a distillation unit bottom streams, a vaporous overhead stream, and a fusel oil stream. A molecular sieve unit is configured to contact a first byproduct stream including at least one selected from a portion of the vaporous overhead stream and a portion of the fusel oil stream. The molecular sieve unit is configured to form a product stream. The molecular sieve unit is configured to be cyclically contacted with at least a portion of the product stream to regenerate the molecular sieve unit and form one or more regenerate streams. A separation system is configured to contact a second byproduct stream including at least one of (1) the regenerate streams and (2) at least a portion of the fusel oil stream, thereby forming a permeate and a retentate. A line is in fluid communication with the separation system to forward at least a portion of the retentate into the product stream.

In certain non-limiting embodiments of the system, the separation system is configured to contact a second byproduct stream including at least one of (1) a portion of the regenerate streams, (2) a portion of the first byproduct stream, (3) a portion of the fusel oil stream, (4) a portion of the vent stream and (5) a portion of the scrubber water, thereby forming a permeate and a retentate. A line is in fluid communication with the separation system to forward at least a portion of the retentate into one of the product stream and the first byproduct stream.

According to another non-limiting aspect of the present disclosure, a membrane unit is configured to contact a stream including at least one of a vaporized first byproduct steam and a portion of the vaporous overhead stream.

BRIEF DESCRIPTION OF THE DRAWINGS

Features and advantages of the processes and systems described herein may be better understood by reference to the accompanying drawings in which.

Figure 1:
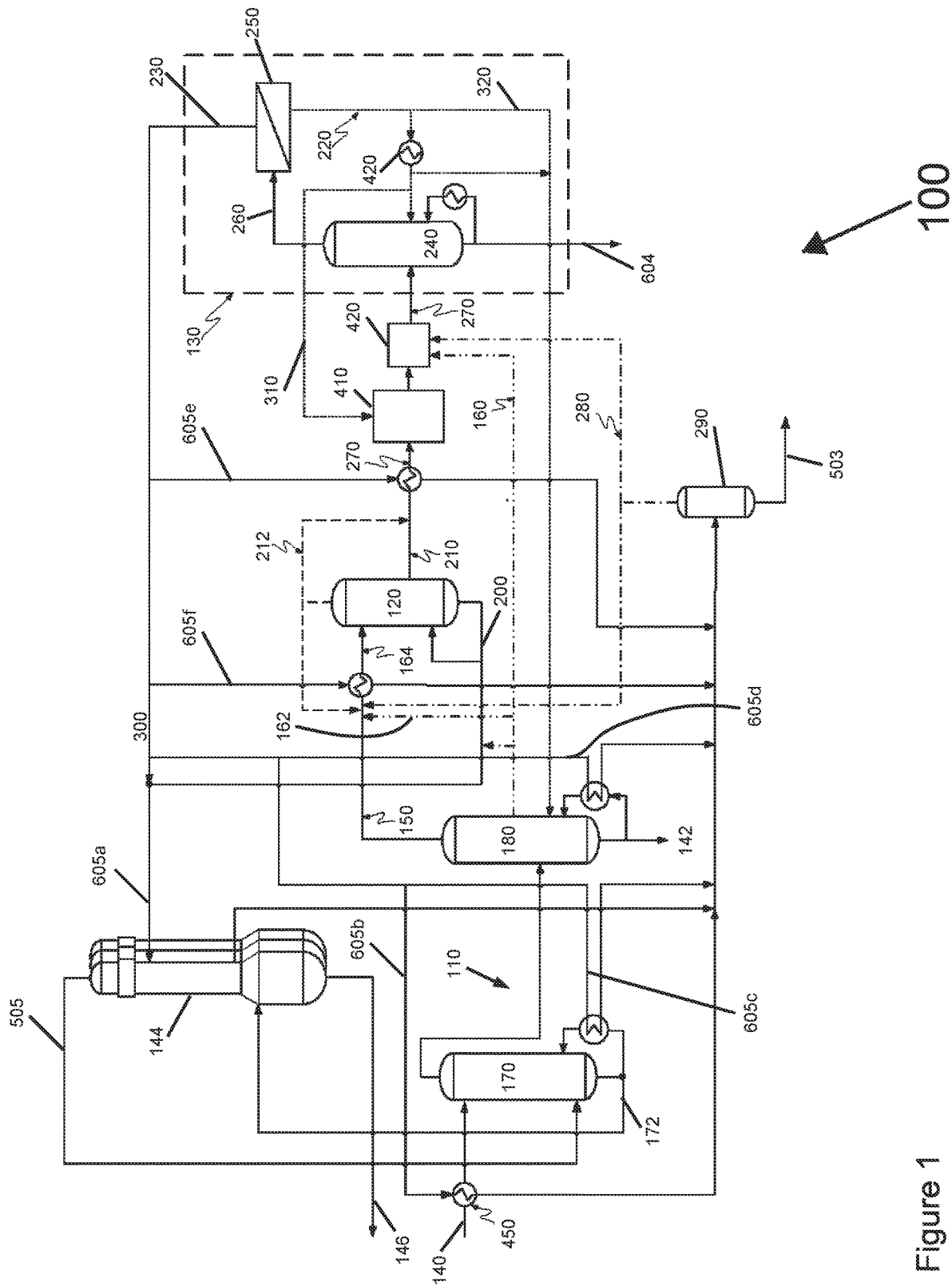
FIG. 1 is a schematic illustration of a non-limiting example embodiment of a system for dehydrating a byproduct stream in ethanol production according to the present disclosure.

The reader will appreciate the foregoing details, as well as others, upon considering the following detailed description of certain non-limiting embodiments of processes and systems according to the present disclosure. The reader may also comprehend certain of such additional details upon using the processes and systems described herein.

DETAILED DESCRIPTION

Prior systems for producing ethanol from feedstock typically require molecular sieve units (MSUs) for dehydrating the feed vapor coming from the stripper/rectifier column or a dedicated vaporizer. The MSUs include two or three beds filled with zeolite pellets, which adsorb water to produce anhydrous vapor until they are saturated with water. While the first bed undergoes a regeneration cycle, the feed vapor coming from the stripper/rectifier column can be switched to a second bed for continued dehydration. A portion of freshly dehydrated alcohol can be redirected into the first bed to remove the water from the saturated zeolite beads, forming a regenerate stream (also referred to as MSU Regen). Due to the water desorption, the regenerate stream (also referred to as MSU Regen) has an ethanol concentration between 50 and 80 vol %, and needs to be recycled to upstream distillation for reprocessing. This operation has a number of disadvantages. For example, as a large portion of ethanol is continuously recycled, (1) capacity in the upstream distillation is used up for dehydrating the MSU Regen, (2) capacity in the MSU itself is used up to essentially dehydrate its own regenerate stream for recycling, and (3) additional energy or steam and cooling water are required for the reprocessing of the MSU Regen. Thus, there has developed a need for processes and systems that overcome the limitations of the process for dehydrating a byproduct stream in ethanol production.

The present disclosure, in part, is directed to processes and systems for dehydrating a byproduct stream in ethanol production. A feed mixture including ethanol and water is distilled with one or more distillation units to remove at least a portion of the water, and form a distillation unit bottom stream, a vaporous overhead stream, and a fusel oil stream. At least a portion of the fusel oil stream is combined with the vaporous overhead stream, thereby producing a first byproduct stream. The first byproduct stream is contacted with a molecular sieve unit, thereby forming a product stream. The molecular sieve unit is cyclically contacted with at least a portion of the product stream to regenerate the molecular sieve unit and form one or more regenerate streams. A second byproduct stream including at least one of (1) the regenerate streams and (2) at least a portion of the fusel oil stream is contacted with a separation system, thereby forming a permeate and a retentate. At least a portion of the permeate is forwarded into the second byproduct stream.

In certain non-limiting embodiments of the method, heat is exchanged between at least a portion of the retentate and the feed mixture. In certain non-limiting embodiments of the method, heat is exchanged between the at least a portion of the retentate and the distillation unit bottom stream. In certain non-limiting embodiments of the method, heat is exchanged between at least a portion of the retentate and the first byproduct stream. In certain non-limiting embodiments of the method, heat is exchanged between at least a portion of the retentate and a portion of the regenerate streams.

In certain non-limiting embodiments of the method, heat is exchanged between at least a portion of the stripper unit bottom stream and at least one selected from the group consisting of the feed mixture, the distillation unit bottom streams, the first byproduct stream, and a portion of the regenerate streams. In certain non-limiting embodiments of the method, heat is exchanged between at least a portion of the regenerate streams and at least one selected from the feed mixture, the distillation unit bottom streams, the first byproduct stream, a feed condensation system, and the second byproduct stream.

Referring to FIG. 1, the illustrated embodiment of the system or production plant 100 for dehydrating a byproduct stream in ethanol production includes a plurality of distillation units 110, an MSU 120, and a separation system 130. The plurality of distillation units 110 are configured to receive a feed mixture 140 including ethanol and water, to remove at least a portion of the water, and form a distillation unit bottom stream 142, vaporous overhead stream 150, and a fusel oil stream 160. A "fusel oil" as used herein includes definitions that are generally known in the chemical engineering art, and can refer to a mixture of high boiling components including propanol, butanol, and isomeric pentanols.

In certain non-limiting embodiments, the distillation unit 110 includes a beer column 170 and a stripper/rectifier column 180. In the beer column 170, the feed mixture 140 is distilled, increasing the ethanol concentration up to 65%. Subsequently, in the stripper/rectifier column 180 the ethanol concentration is further increased to around 90 vol %. In certain non-limiting embodiments, the beer column 170 forms a beer column stillage stream 172, and heat is exchanged between the beer column stillage stream 172 and the retentate, as further explained below. Although FIG. 1 illustrates the system 100 as including two distillation units 170, 180, in other embodiments, the system 100 may include a single distillation unit or may include three or more distillations units.

In certain non-limiting embodiments, the distillation units 110 are in fluid communication with one or more evaporators 144, which form an evaporator stillage stream 146. For example, the system 100 can include two or more, three or more, four or more, five or more, six or more, seven or more, or eight or more evaporators 144. The process and system described herein are not limited in this regard. As further explained below, heat can be exchanged in the evaporators 144 between the beer column stillage stream 172 and at least one selected from the MSU product steam and the retentate (which are condensed). The beer column stillage stream 172 can have a solids content of approximately 7%. By exchanging heat between the beer column stillage stream 172 and the MSU product stream and/or retentate, some of the water in the beer column stillage stream 172 can be evaporated, which can increase the solids content to become a thick stillage as the stillage travels through the evaporators 144, forming the evaporator stillage stream 146 with a solids content of approximately 35%.

In certain non-limiting embodiments, at least a portion of the fusel oil stream 160 (e.g., the vaporous portion of the fusel oil stream 162) is combined with the vaporous overhead stream 150, thereby producing a first byproduct stream 164. In certain non-limiting embodiments, the first byproduct stream 164 includes only the vaporous overhead stream 150 and not the fusel oil stream 160. The MSU 120 includes one ore more beds, and is configured to contact the first byproduct stream 164 to form a product stream 200.

With continuing reference to FIG. 1, the MSU 120 is cyclically contacted with at least a portion of the product stream 200 to regenerate itself and form the MSU regenerate streams 210, 212. Although FIG. 1 illustrates the MSU 120 as forming two MSU regenerate streams 210, 212, in other embodiments the MSU 120 can form a single stream. In some embodiments, the first MSU regenerate stream 210 is a water-rich stream (e.g., having approximately 50% water and approximately 50% ethanol), and the second MSU regenerate stream 212 is a water-lean stream (e.g., having approximately 3% water and approximately 97% ethanol). The regeneration of the MSU 120 is a discontinuous desorption process, gradually removing the water by passing at least a portion of the product stream 200 through the bed at a substantially lower pressure (i.e., a vacuum) than was used for loading the bed for the dehydration step. There are both high pressure and low pressure molecular sieve systems; the regeneration of each involves use of a relative vacuum along with anhydrous ethanol in the regeneration step. Referring to FIG. 1, in the illustrated embodiment at least a portion of one of the second MSU regenerate stream 212 is forwarded into the first byproduct stream 164. In another embodiment, all of the second MSU regenerate stream 212 can be forwarded in a direction away from the MSU 120.

In certain non-limiting embodiments, the separation system 130 is configured to contact a second byproduct stream 270 including at least one of (1) the MSU regenerate streams 210, 212, and (2) at least a portion of the fusel oil stream 160, thereby forming a permeate 220 and a retentate 230. In certain non-limiting embodiments, at least a portion of the retentate 230 is forwarded into the product stream 200 via a retentate line 300. In certain non-limiting embodiments, a first portion of the permeate 220 is forwarded into the separation system 130 via a first permeate line 310, and a second portion of the permeate 220 is forwarded into at least one of the distillation units 170, 180 via a second permeate line 320. In some embodiments, the first portion of the permeate 220 is condensed before being forwarded into the separation system 130. In some embodiments, the first portion of the permeate 220 is condensed and combined with the second byproduct stream 270 before being forwarded into the separation system 130. In some embodiments, the second portion of the permeate 220 is condensed before being forwarded to at least one of the distillation units 110. In some embodiments, the second portion of the permeate 220 is forwarded into at least one of the distillation units 110 via direct vapor injection.

In certain non-limiting embodiments, the second byproduct stream 270 includes at least a portion of the fusel oil stream 160. In some embodiments, the second byproduct stream 270 is blended with at last a portion of an overhead vent stream 280 before being contacted with the separation system 130. For example, a flash tank 290 is in fluid communication with the MSU 120, and forms the overhead vent stream 280. A "vent stream" as used herein includes definitions that are generally known in the chemical engineering art, and can refer to a flash recycle stream resulting from the condensation of an MSU product. In certain non-limiting embodiments, at least portion of the overhead vent stream 280 is forwarded into the first byproduct stream 164. In certain non-limiting embodiments, at least portion of the overhead vent stream 280 is forwarded into the separation system via tank 420 where the energy available in vent stream 280 can be recovered.

In certain non-limiting embodiments, the separation system 130 includes a stripper/vaporizer unit 240 and a membrane 250. The stripper/vaporizer unit 240 is configured to receive at least one of the fusel oil stream 160 and the MSU regenerate streams 210, 212 and form a membrane feed vapor 260, and the membrane 250 is configured to contact the membrane feed vapor 260, thereby forming the permeate 220 and the retentate 230. In certain non-limiting embodiments, the stripper/vaporizer unit 240 is a stripper unit; in other embodiments, the stripper/vaporizer unit 240 is a vaporizer unit. A stripper unit forms a pure water bottom stream, whereas a vaporizer unit forms only enriched ethanol vapors substantially without any bottom stream. In certain non-limiting embodiments, the permeate 220 is forwarded into the stripper unit 240 of the separation system 130.

In certain non-limiting embodiments, the separation system 130 is pressurized (e.g., to at least 0.3 MPa), thereby heating the retentate 230. The heat contained in the vaporous retentate 230 is recuperated in an upstream heat exchanger (e.g., MSU superheater) to reduce the overall energy consumption of the entire distillation/dehydration section of the plant 100, as further explained below.

In certain non-limiting embodiments, the membrane 250 is a polymer membrane built on a hollow fiber backbone. In certain non-limiting embodiments, a selective layer is placed on either the outside (shell side) or inside (lumen side) of the hollow fibers. In other embodiments, the membrane 250 may assume any other form, for example including zeolites as adsorbents, so long as the membrane 250 can dehydrate the membrane feed vapor 260 to certain water contents depending on the usage requirements or preferences for the particular system 100.

In certain non-limiting embodiments, the second byproduct stream 270 defines an azeotropic ethanol concentration. An "azeotropic mixture" as used herein includes definitions that are generally known in the chemical art, and can refer to a mixture of two or more liquids in such a way that its components cannot be altered by simple distillation.

In certain non-limiting embodiments, the retentate 230 has an ethanol concentration higher than the azeotropic ethanol concentration.

In certain non-limiting embodiments, the separation system 130 can be pre-assembled as a unit. In this way, the separation system 130 can be installed to new systems 100 at final assembly, or retrofitted to existing plants that use extractive distillation with such separation systems. In certain non-limiting embodiments, the separation system 130 is integrated without additional power (e.g., electricity) requirement, and the retentate 230 is discharged by pressure without any power supply.

The main benefits of the dedicated separation system 130 are that it (1) frees up capacity in the main distillation, (2) reduces load to the MSU, and (3) significantly reduces the overall energy consumption of the distillation/dehydration section. Another benefit of the dedicated separation system 130 is that the freed-up capacity in the distillation units 110 and the MSU 120 can be used to increase overall production capacity, as the amount of the ethanol that was previously recycled as MSU regenerate streams can be supplied through the beer column 170. For example, the capacity of the plant 100 can be increased up to 30% without size changes to the stripper/rectifier column 180 or the MSU 120 and without increasing energy consumption. Depending on the usage requirements or preferences for the particular plant 100, the separation system 130 can avoid the recirculation of the MSU regenerate streams 210, 212 into the stripper/rectifier column 180, rendering the distillation units 110 less prone to fluctuations and allowing a more efficient operation.

In certain non-limiting embodiments, the energy contained in the retentate 230 can be recuperated in the plant 100. Put another way, the plant 100 can provide upstream heat integration. In certain non-limiting embodiments, heat is exchanged between at least a portion of the retentate 230 and at least one selected from the feed mixture 140, the distillation unit bottom stream 142, the first byproduct stream 164, and a portion of the MSU regenerate streams 210, 212. In certain non-limiting embodiments, the heat exchange can be achieved via tie-ins of lines or a heat recovery unit configured to receive at least a portion of the retentate 230 and at least one selected from the feed mixture 140, the distillation unit bottom stream 142, the first byproduct stream 164, the beer column stillage stream 172, and a portion of the MSU regenerate streams 210, 212. The result of this heat integration is that energy savings in the main process are larger than the additional energy consumption of the separation system 130 (e.g., 30% or more), thereby reducing the overall energy consumption of the plant 100 in a compact footprint.

Referring to FIGS. 2-5, in the illustrated embodiments a scrubbing system 105 is used to remove ethanol from vent gases (e.g., $CO_2$, with traces of ethanol) from the fermentation stream removing the ethanol before venting $CO_2$ to the atmosphere. Scrubber water is added in the scrubbing system generating a water stream 107 containing small amounts of ethanol which is directed to the beer well prior to being fed to the beer column. At least a portion of the product stream is forwarded to a flash vessel 290, thereby forming a vent stream 503. A second byproduct stream 270 including at least one of (1) a portion of the regenerate streams 210a, 210b, 307, (2) a portion of the first byproduct stream 164a and 164b, (3) a portion of the fusel oil stream 160a and 160b, (4) a portion of the vent stream 503 and (5) a portion of the scrubber water 107 is contacted with the separation system 240, 250, and 420, thereby forming the permeate 220, the retentate 230, and a stripper unit bottom stream 604. In certain non-limiting embodiments of the method, heat is exchanged between a portion of the retentate 605b and the feed mixture to the beer column. In another embodiment, heat is exchanged between a portion of the retentate 605c, 605d, 605g and the distillation unit bottom streams. In another embodiment, heat is exchanged between a portion of the retentate 605f and the first byproduct stream. In another embodiment, heat is exchanged between a portion of the retentate 605a and evaporators 144. In another embodiment, heat is exchanged between a portion of the retentate 605e and a portion of the regenerate streams.

Figure 2:
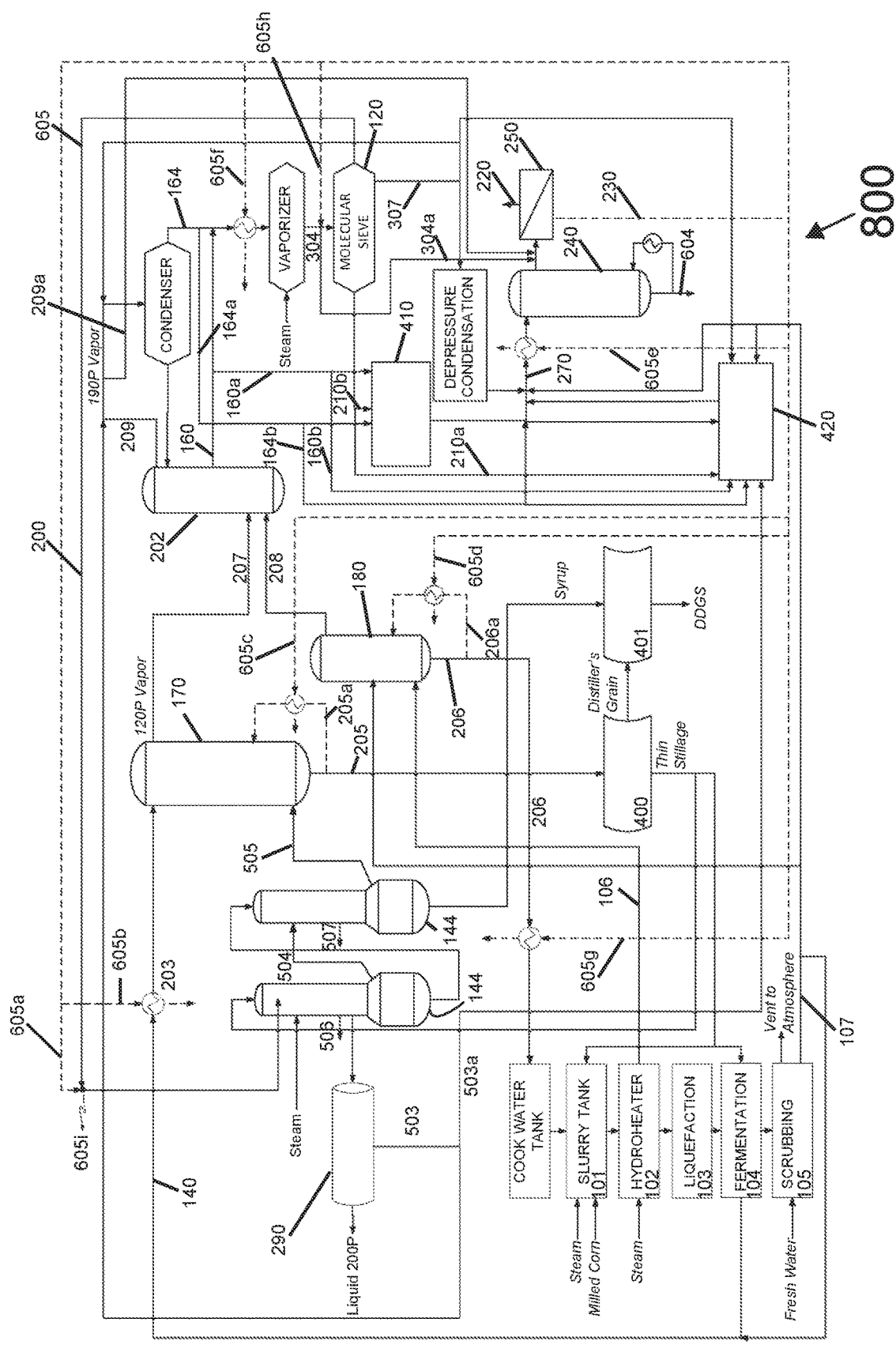
FIG. 2 is a schematic illustration of another non-limiting example embodiment of a system for dehydrating a byproduct stream in ethanol production according to the present disclosure.

With continuing reference to FIG. 2, in the illustrated embodiment steam generated in at least one of (1) evaporators 505, (2) a hydroheater 106, and (3) a boiler is injected to the distillation units as energy source for their operation. The steam injected in the distillation units increases the water content and dilutes the solids contained in the distillation unit bottom streams. The solids in distillation unit bottom streams are recovered in at least one selected from a centrifuge 400, a dryer 401, and the evaporators 144. In certain non-limiting embodiments of the method, at least a portion of the steam injected on the distillation units is replaced by reboiling at least one selected from a portion of the beer column stillage stream 205 and the stripper-rectifier bottom stream 206. A benefit of the reboilers is that energy savings can be up to 30%, and the capacity of the plant 800 can be increased up to 30% without size changes to the stripper/rectifier column and without increasing energy consumption.

Figure 3:
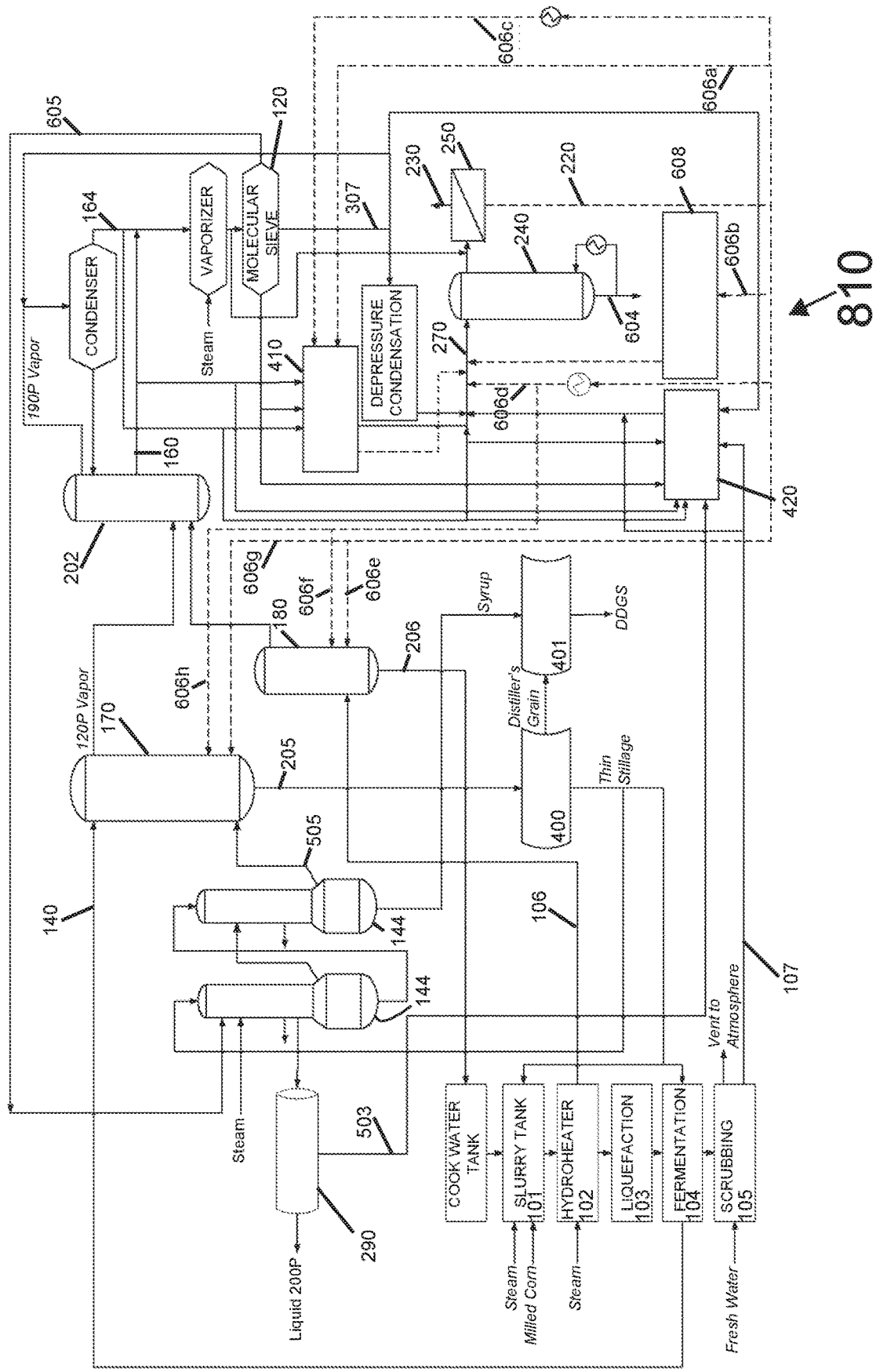
FIG. 3 is a schematic illustration of yet another non-limiting example embodiment of a system for dehydrating a byproduct stream in ethanol production according to the present disclosure.

Referring to FIG. 3, in the illustrated embodiment the vapor permeate 220 can be integrated into the second byproduct stream. In certain non-limiting embodiments of the method, a portion of the permeate 606a is forwarded into the second byproduct stream via the regenerate condensation vacuum system 410. In another embodiment, a portion of the permeate 606b is forwarded into the second byproduct stream via the permeate condensation vacuum system 608. The permeate condensation system is designed to condense the vapor permeate and to generate the vacuum required by the membrane unit 250 in the separation system. In another embodiment, a portion of the permeate 606d is forwarded into the second byproduct stream via direct contact. In another embodiment, a portion of the permeate 606e, 606f, 606g, 606h is forwarded into the second byproduct stream via the distillation units. In certain non-limiting embodiments of the method, a portion of the permeate 606c is forwarded into the second byproduct stream via the regenerate condensation vacuum system 410 after being condensed in a separate heat exchanger.

Figure 4:
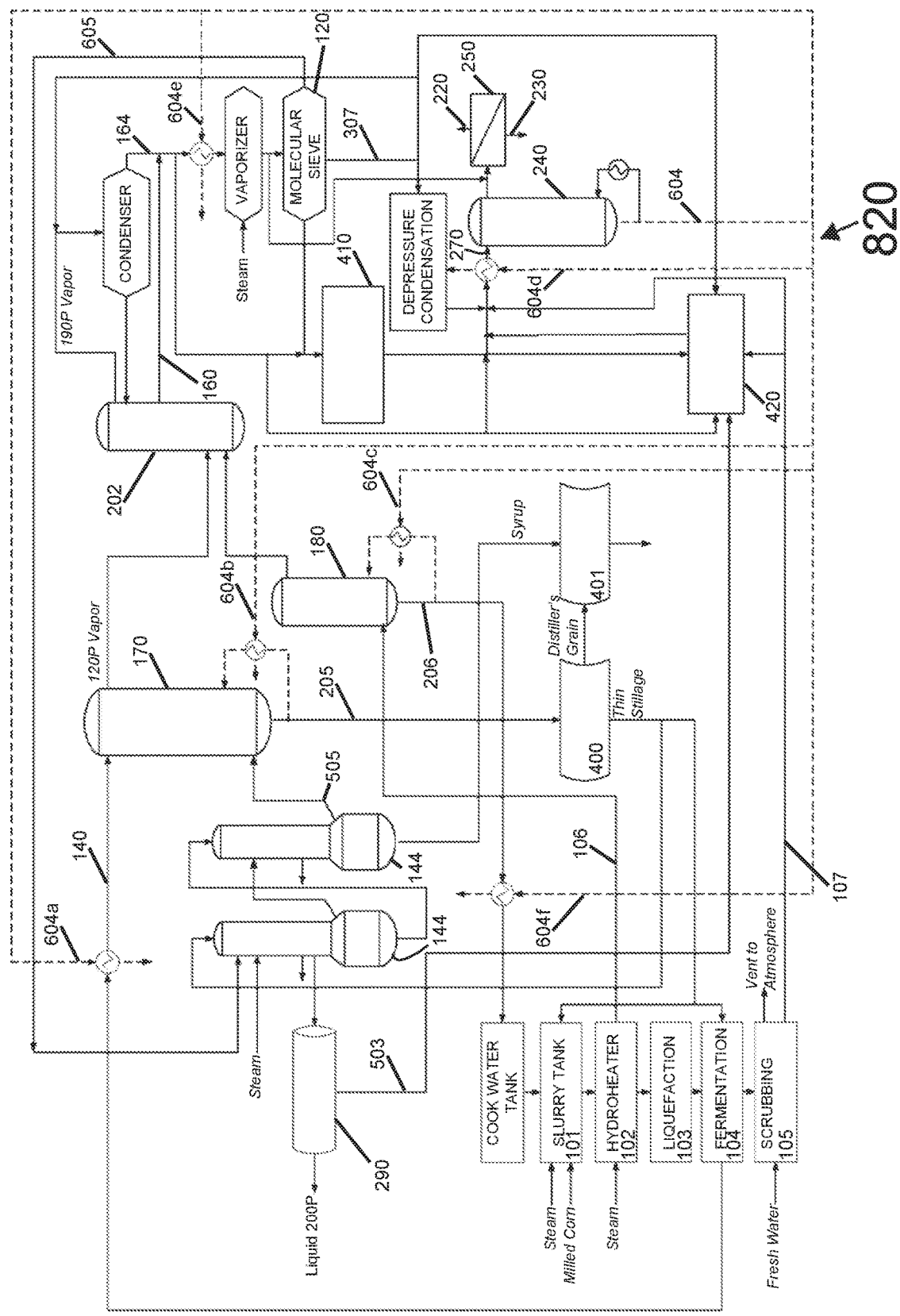
FIG. 4 is a schematic illustration of yet another non-limiting example embodiment of a system for dehydrating a byproduct stream in ethanol production according to the present disclosure.

Referring to FIG. 4, in the illustrated embodiment the plant 820 can provide heat integration from the stripper unit bottom stream. In certain non-limiting embodiments of the method, heat is exchanged between a portion of the stripper unit bottom stream 604a and the feed mixture. In another embodiment, heat is exchanged between a portion of the stripper unit bottom stream 604b, 604c, and 604f and the distillation unit bottom streams. In another embodiment, heat is exchanged between a portion of the stripper unit bottom stream 604e and the first byproduct stream. In another embodiment, heat is exchanged between a portion of the stripper unit bottom stream 604d and a portion of the regenerate streams.

Figure 5:
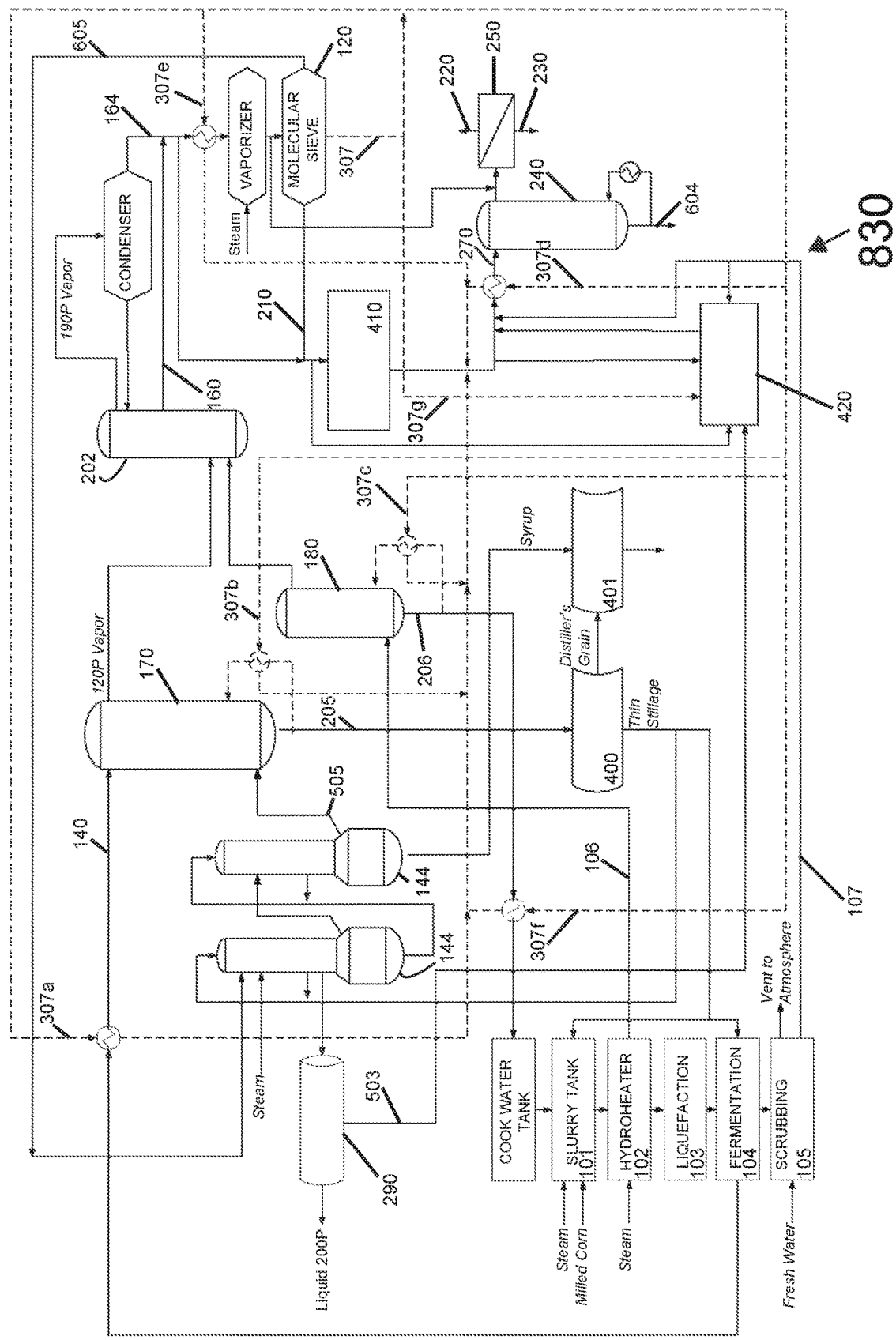
FIG. 5 is a schematic illustration of yet another non-limiting example embodiment of a system for dehydrating a byproduct stream in ethanol production according to the present disclosure.

Referring to FIG. 5, in the illustrated embodiment the plant 830 can provide heat integration from at least one of the regenerate streams (also referred to as Depressure stream). In certain non-limiting embodiments of the method, heat is exchanged between a portion of the Depressure stream 307a and the feed mixture. In another embodiment, heat is exchanged between a portion of the Depressure stream 307b, 307c, and 307f and the distillation unit bottom streams. In another embodiment, heat is exchanged between a portion of the Depressure stream 307e and the first byproduct stream. In another embodiment, heat is exchanged between a portion of the Depressure stream 307g and a feed condensation system 420 which is designed to recover the energy available in vaporous streams including the Depressure stream. In another embodiment, heat is exchanged between a portion of the Depressure stream and the second byproduct stream 270 via heat exchangers 307d.

Figure 6:
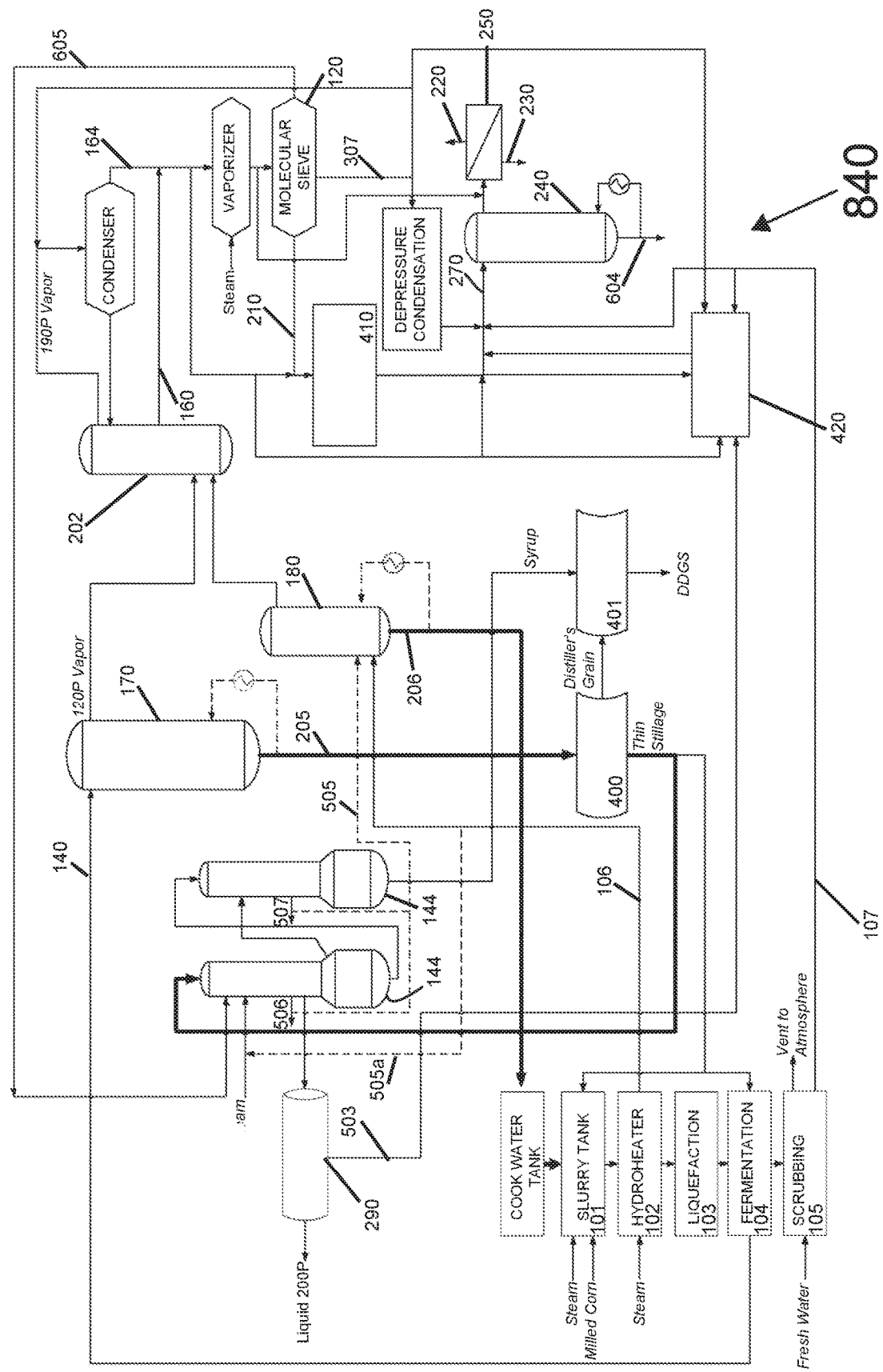
FIG. 6 is a schematic illustration of yet another non-limiting example embodiment of a system for dehydrating a byproduct stream in ethanol production according to the present disclosure.

Referring to FIG. 6, in the illustrated embodiment the energy displaced in the distillation units by forwarding at least a portion of the regenerate streams into the second byproduct stream allows to forward (1) at least a portion of the steam 505a from the hydroheater into the evaporators, and (2) steam 506a from the evaporators to the distillation unit. A benefit of this energy re-balancing of the plant 100 is that energy savings may be 30% or higher, and the capacity of the plant 100 may be increased 30% or higher without size changes to the stripper/rectifier column and without increasing energy consumption.

Figure 7:
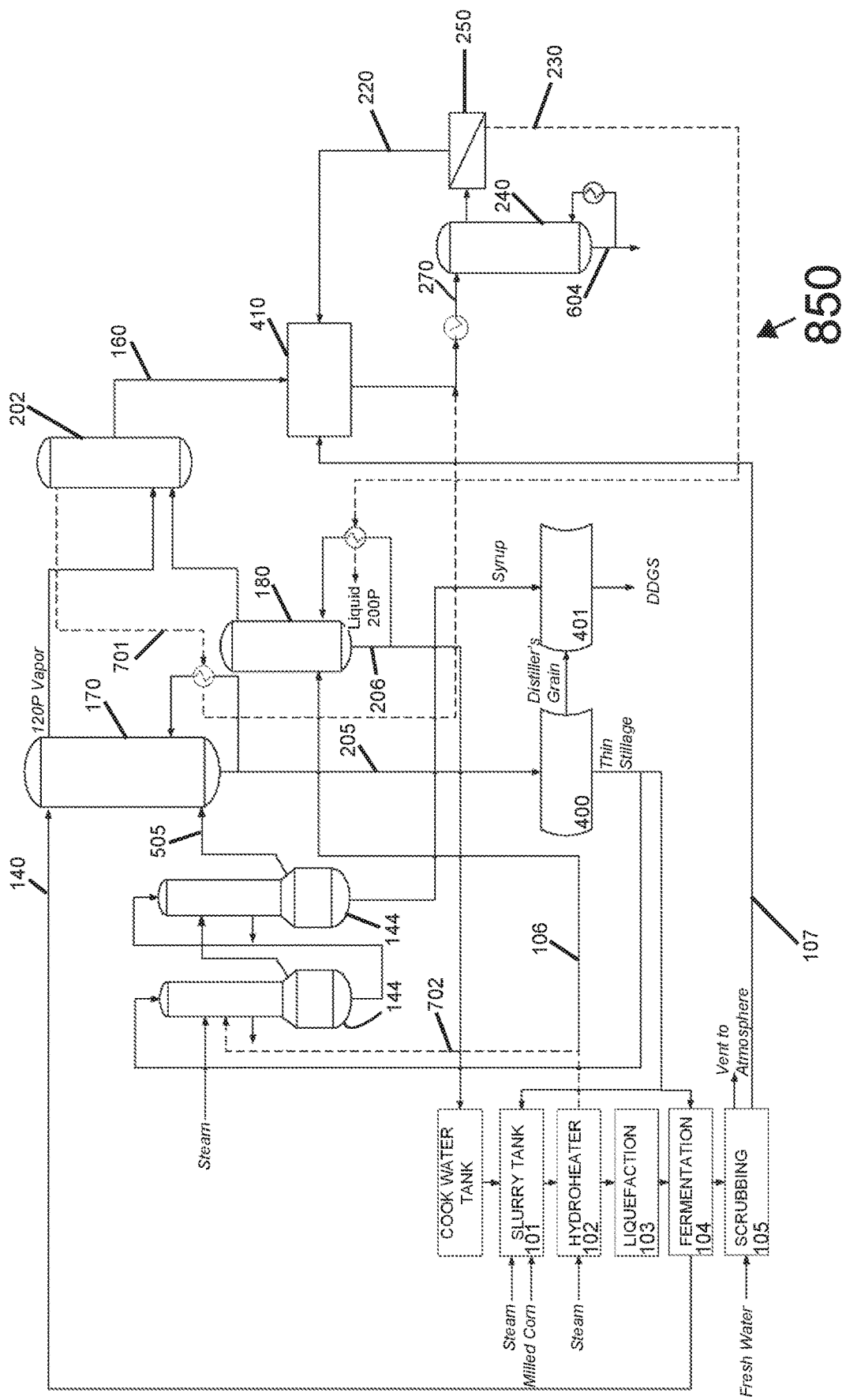
FIG. 7 is a schematic illustration of yet another non-limiting example embodiment of a system for dehydrating a byproduct stream in ethanol production according to the present disclosure.

Referring to FIG. 7, in the illustrated embodiment the rectifier column 202 operates as a stripper column, thereby eliminating the need of a 190-proof ethanol vapor condenser and reducing the cooling water consumption. The beer column reboiler is operated with the overhead stream 701 from the rectifier column 202. The condensed overhead stream is processed in the separation system 240, 250. The energy in the retentate 230 is used to operate the side stripper reboiler. The evaporators are operated at least in part with the steam 702 from the hydroheater, as the side stripper no longer needs the steam 702 from the hydroheater.

Although the foregoing description has necessarily presented only a limited number of embodiments, those of ordinary skill in the relevant art will appreciate that various changes in the processes and systems other details of the examples that have been described and illustrated herein may be made by those skilled in the art, and all such modifications will remain within the principle and scope of the present disclosure as expressed herein and in the appended claims. For example, although the present disclosure has presented only a limited number of embodiments of heat integration, it will be understood that the present disclosure and associated claims are not so limited. Those having ordinary skill will readily identify additional heat integration schemes along the lines and within the spirit of the necessarily limited number of embodiments discussed herein. It is understood, therefore, that the present inventions are not limited to the particular embodiments disclosed herein, but is intended to cover modifications that are within the principle and scope of the inventions, as defined by the claims. It will also be appreciated by those skilled in the art that changes could be made to the embodiments above without departing from the broad inventive concept thereof.

In the present description of non-limiting embodiments and in the claims, other than in in the operating examples or where otherwise indicated, all numbers expressing quantities or characteristics of ingredients and products, processing conditions, and the like are to be understood as being modified in all instances by the term "about." Accordingly, unless indicated to the contrary, any numerical parameters set forth in the following description and the attached claims are approximations that may vary depending upon the desired properties one seeks to obtain in the processes and systems according to the present disclosure. At the very least, and not as an attempt to limit the application of the doctrine of equivalents to the scope of the claims, each numerical parameter should at least be construed in light of the number of reported significant digits and by applying ordinary rounding techniques.

We claim:

1. A method of dehydrating a byproduct stream in ethanol production, the method comprising:
    distilling a feed mixture including ethanol and water with a distillation unit to remove at least a portion of the water, and form a distillation unit bottom stream, a vaporous overhead stream, and a fusel oil stream;
    contacting a molecular sieve unit with a first byproduct stream comprising at least one selected from the group consisting of a portion of the vaporous overhead stream and a portion of the fusel oil stream, thereby forming a product stream;
    cyclically contacting the molecular sieve unit with at least a portion of the product stream to regenerate the molecular sieve unit, and form a regenerate stream;
    contacting a second byproduct stream comprising at least one of (1) the regenerate stream and (2) at least a portion of the fusel oil stream with a separation system, thereby forming a permeate and a retentate;
    forwarding at least a portion of the retentate into the product stream; and
    exchanging heat between at least a portion of the regenerate stream and at least one selected from the feed mixture, the distillation unit bottom streams, the first byproduct stream, the contents of a tank, and the second byproduct stream.

2. The method of claim 1, wherein the distillation unit comprises a beer column and a stripper-rectifier column in fluid communication with the beer column, wherein the beer column forms a beer column stillage stream, and wherein heat is exchanged between the at least a portion of the retentate and the beer column stillage stream.

3. The method of claim 2, wherein the distillation unit is in fluid communication with an evaporator, wherein the evaporator forms an evaporator stillage stream, and wherein a second portion of the retentate is forwarded into the evaporator.

4. The method of claim 1, wherein the molecular sieve unit forms only a single regenerate stream.

5. The method of claim 1, wherein the regenerate stream further comprises a water-rich first stream and a water-lean second stream.

6. The method of claim 1, wherein at least a portion of the regenerate stream is forwarded into the first byproduct stream.

7. The method of claim 1, wherein a first portion of the permeate is returned to the separation system, or a second portion of the permeate is returned to the distillation unit.

8. The method of claim 7, wherein the first portion of the permeate is returned to the separation system and is condensed before being returned to the separation system.

9. The method of claim 7, wherein the first portion of the permeate is returned to the separation system and is condensed and combined with the second byproduct stream before being returned to the separation system.

10. The method of claim 7, wherein the second portion of the permeate is returned to the distillation unit and is condensed before being returned to the distillation unit.

11. The method of claim 7, wherein the second portion of the permeate is returned into the distillation unit via direct vapor injection.

12. The method of claim 1, wherein the second byproduct stream comprises at least a portion of the fusel oil stream.

13. The method of claim 1, wherein a flash tank is in fluid communication with the molecular sieve unit, wherein the flash tank forms an overhead vent stream, and wherein the second byproduct stream is blended with at least a portion of the overhead vent stream before being contacted with the separation system.

14. The method of claim 13, wherein at least a portion of the overhead vent stream is forwarded into the first byproduct stream.

15. The method of claim 13, wherein the separation system comprises a stripper unit and a membrane, the stripper unit receiving at least one of the fusel oil stream, the regenerate stream and the overhead vent stream, and forming a membrane feed vapor, and the membrane contacting the membrane feed vapor, thereby forming the permeate and the retentate.

16. The method of claim 15, wherein the permeate is forwarded into the stripper unit of the separation system.

17. The method of claim 13, wherein the separation system comprises a vaporizer and a membrane, the vaporizer receiving at least one of the fusel oil stream, the regenerate stream and the overhead vent stream, and forming a membrane feed vapor, and the membrane contacting the membrane feed vapor, thereby forming the permeate and the retentate.

18. A method of dehydrating a byproduct stream in ethanol production, the method comprising:
  distilling a feed mixture including ethanol and water with at least two distillation units including a beer column in fluid communication with a first stripper-rectifier column to remove at least a portion of the water from the feed mixture, the beer column forming a beer column stillage stream and a beer column vaporous overhead stream, and the first stripper-rectifier column forming a first stripper-rectifier bottom stream and a first stripper-rectifier vaporous overhead stream;
  reboiling a portion of the beer column stillage stream to produce a first supplemental steam, wherein reboiling the portion of the beer column stillage stream is driven by heat supplied by a retentate, a bottom stream of a stripper/vaporizer of a separation system, a depressure stream formed by a molecular sieve unit, or a second stripper-rectifier vaporous overhead stream formed by a second stripper-rectifier column in fluid communication with the beer column and the first stripper-rectifier column;
  forwarding the first supplemental steam to the beer column; and
  reboiling a portion of the stripper-rectifier bottom stream to produce a second supplemental steam;
  forwarding the second supplemental steam to the stripper-rectifier column.

19. The method of claim 18, further comprising:
  contacting the molecular sieve unit with a first byproduct stream comprising at least one selected from the group consisting of a portion of the first stripper-rectifier vaporous overhead stream and a portion of the first fusel oil stream, thereby forming a product stream;
  cyclically contacting the molecular sieve unit with at least a portion of the product stream to regenerate the molecular sieve unit, and form a regenerate stream;
  contacting a second byproduct stream comprising at least one of (1) the regenerate stream and (2) at least a portion of the first fusel oil stream with the separation system, thereby forming a permeate and the retentate; and
  forwarding at least a portion of the retentate into the product stream.

20. The method of claim 19, further comprising exchanging heat between at least a portion of the regenerate stream and the first stripper-rectifier bottom stream.

21. The method of claim 18, wherein reboiling the portion of the beer column stillage stream is driven by heat supplied by the bottom stream of a stripper/vaporizer of a separation system, the depressure stream formed by a molecular sieve unit, or the second stripper-rectifier vaporous overhead stream formed by the second stripper-rectifier column in fluid communication with the beer column and the first stripper-rectifier column.

22. The method of claim 18, further comprising forwarding the first stripper-rectifier vaporous overhead stream to the second stripper-rectifier column, and forwarding a second fusel oil stream formed by the second stripper-rectifier column to the separation system.

23. The method of claim 18, wherein reboiling the portion of the stripper-rectifier bottom stream is driven by heat supplied by the retentate, the bottom stream of the stripper/vaporizer of the separation system, or the depressure stream formed by a molecular sieve unit.

* * * * *